(12) United States Patent
Ansai et al.

(10) Patent No.: US 8,710,262 B2
(45) Date of Patent: Apr. 29, 2014

(54) METHOD FOR PRODUCING (METH)ACRYLIC ANHYDRIDE, METHOD FOR STORING (METH)ACRYLIC ANHYDRIDE, AND METHOD FOR PRODUCING (METH)ACRYLATE

(71) Applicant: Mitsubishi Rayon Co., Ltd., Tokyo (JP)

(72) Inventors: Ryuichi Ansai, Otake (JP); Hiroyuki Nogami, Otake (JP); Kuniyoshi Ogura, Otake (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 14/016,764

(22) Filed: Sep. 3, 2013

(65) Prior Publication Data
US 2014/0005435 A1 Jan. 2, 2014

Related U.S. Application Data (62) Division of application No. 13/057,576, filed as application No. PCT/JP2009/063812 on Aug. 4, 2009, now Pat. No. 8,586,791.

(30) Foreign Application Priority Data

Aug. 5, 2008 (JP) .................. 2008-201857
Aug. 7, 2008 (JP) .................. 2008-204452

(51) Int. Cl.
*C07C 65/00* (2006.01)
*C07C 51/56* (2006.01)

(52) U.S. Cl.
USPC ........................ 562/887; 562/888; 562/894

(58) Field of Classification Search
None
See application file for complete search history.

(56) References Cited

U.S. PATENT DOCUMENTS

| 4,830,789 A | 5/1989 | Hinenoya et al. |
| 6,936,734 B2 | 8/2005 | Schmitt et al. |
| 2003/0018217 A1 | 1/2003 | Dupont et al. |

FOREIGN PATENT DOCUMENTS

| CN | 1396149 A | 2/2003 |
| JP | 54 135706 | 10/1979 |
| JP | 62 181231 | 8/1987 |
| JP | 2000 191590 | 7/2000 |
| JP | 2002 275124 | 9/2002 |
| JP | 2003 40832 | 2/2003 |

OTHER PUBLICATIONS

International Search Report Issued Nov. 2, 2009 in PCT/JP09/063812 filed Aug. 4, 2009.
Chinese Office Action Issued Nov. 5, 2012 in Patent Application No. 200980129104.X (with Partial English translation).

*Primary Examiner* — Yevegeny Valenrod
(74) *Attorney, Agent, or Firm* — Oblon, Spivak, McClelland, Maier & Neustadt, L.L.P.

(57) ABSTRACT

It is an object of the present invention to provide a method for producing (meth)acrylic anhydride that provides high yield and high efficiency and can suppress side reactions, in a method for reacting (meth)acrylic acid with a fatty acid anhydride to produce (meth)acrylic anhydride. The method for producing (meth)acrylic anhydride according to the present invention is a method for producing (meth)acrylic anhydride, including reacting a fatty acid anhydride with (meth)acrylic acid to produce (meth)acrylic anhydride, while extracting a fatty acid produced as a by-product, wherein the reaction is performed, while adjustment is performed so that a molar ratio of the (meth)acrylic acid to the (meth)acrylic anhydride in a reaction liquid is 0.3 or more.

4 Claims, 1 Drawing Sheet

US 8,710,262 B2

METHOD FOR PRODUCING (METH)ACRYLIC ANHYDRIDE, METHOD FOR STORING (METH)ACRYLIC ANHYDRIDE, AND METHOD FOR PRODUCING (METH)ACRYLATE

CROSS REFERENCE TO RELATED APPLICATIONS

This application is a divisional of U.S. patent application Ser. No. 13/057,576, filed on Feb. 4, 2011, the entire content of which is incorporated herein by reference, and which is a 35 U.S.C. §371 national stage patent application of international patent application PCT/JP09/063,812, filed Aug. 4, 2009, and claims the benefit of the Japanese patent application JP 2008-201857, filed Aug. 5, 2008 and the Japanese patent application JP 2008-204452, filed Aug. 7, 2008.

TECHNICAL FIELD

The present invention relates to a method for reacting (meth)acrylic acid with a fatty acid anhydride to produce (meth)acrylic anhydride, and a method for storing (meth)acrylic anhydride. The present invention also relates to a method for reacting (meth)acrylic anhydride with an alcohol to produce a (meth)acrylate.

BACKGROUND ART

As a method for reacting (meth)acrylic acid with a fatty acid anhydride to produce (meth)acrylic anhydride, Patent Literature 1 describes a method for producing (meth)acrylic anhydride from (meth)acrylic acid and acetic anhydride, using a catalyst, such as sodium acetate, while removing acetic acid produced as a by-product. Patent Literature 2 describes a method for introducing acetic anhydride and/or (meth)acrylic acid into a reaction medium, while removing acetic acid produced as a by-product, to at least partially replace the removed acetic acid.

In both of these methods, the reaction is completed within 10 hours. But, the acetic anhydride is used on a scale of several tons in industrial terms, and therefore, a longer time is required to extract the acetic acid produced as a by-product. Acetic acid, acetic anhydride, and (meth)acrylic acid have a close vapor pressure at each temperature, and therefore, a rectifying column having a large theoretical plate number and a large inner diameter is required to separate the acetic acid from a mixture of these by rectification. But, the size of the distillation column is restricted due to location and structural problems, and therefore, a method for increasing the reflux ratio to enhance purification efficiency is adopted. In this case, most of the distillate is returned to the distillation column, and therefore, the extraction efficiency of the acetic acid decreases significantly, and the reaction time must be long.

For example, a method for reacting a liquid using 763 g of acetic anhydride in 3 hours, using an apparatus in which a 4 L glass flask is equipped with a distillation attachment having a diameter of 50 mm and a packing height of 850 mm, is described in Example 4 in Patent Literature 3. The purification efficiency is enhanced by returning 80 percent or more of the distillate to the distillation column, which corresponds to a reflux ratio of 5:1, but the distilled acetic acid contains 8.5% acetic anhydride.

From the study of the present inventors, it has been found that in the reaction, side reactions, such as the degradation reaction of (meth)acrylic anhydride, the multimerization of the (meth)acrylic anhydride, and the Michael addition of methacrylic acid, proceed. In the conventional method, these side reactions have not been considered as a problem, for the reasons that the amount of the side reaction products is small because the reaction time is short, that the analysis method is imperfect, and the like. But, from the study of the present inventors, it has been found that as the reaction time increases, the effect of the side reactions increases, and the decrease in yield and purity becomes significant. Further, it has been found that side reactions, such as the degradation reaction of (meth)acrylic anhydride, the multimerization of (meth) acrylic anhydride, and the Michael addition of methacrylic acid, proceed during storage of (meth)acrylic anhydride, and the purity decreases over time.

(Meth)acrylic anhydride is used for a raw material when being reacted with alcohols to produce (meth)acrylates. But, if such (meth)acrylic anhydride with a large amount of by-products is used, the by-products are reacted with the alcohols, and therefore, the purity and yield of the (meth)acrylates decrease.

A method for reacting (meth)acrylic anhydride with an alcohol is known as a method for producing a (meth)acrylate. Patent Literature 1 describes a method for reacting (meth) acrylic anhydride with phenols, as a method for producing phenyl(meth)acrylate. But, in the method described in Patent Literature 1, almost the same moles of (meth)acrylic acid produced as a by-product as the (meth)acrylic anhydride used is removed by washing with an aqueous sodium hydroxide solution and water. In this method, a large amount of the (meth)acrylic acid is disposed of, and therefore, resources are wasted, and in addition, the load of wastewater treatment is large.

Methods for recovering, from a reaction liquid containing a compound that can be used as a raw material, the raw material, and using it again are generally performed. Usually, these methods are carried out in a one-stage reaction, and therefore, even if the product is mixed in the recovered raw material, no problem occurs.

On the other hand, in the case of a reaction carried out in two stages, such as synthesizing (meth)acrylic anhydride and reacting the (meth)acrylic anhydride with phenol to produce phenyl(meth)acrylate, in a method for producing phenyl (meth)acrylate, the phenyl(meth)acrylate and a compound having a phenolic hydroxyl group are present in the second-stage reaction. These compounds are compounds that are not originally present in the first-stage reaction.

If (meth)acrylic acid produced as a by-product in the second stage is recovered by a usual method and reused in the first-stage reaction, by-products, such as phenyl acetate, are produced in the first-stage reaction because this (meth)acrylic acid contains phenyl(meth)acrylate, phenol, and the like, and the purity of (meth)acrylic anhydride decreases. Further, the purity and yield of phenyl(meth)acrylate obtained by this (meth)acrylic anhydride decrease.

From the study of the present inventors, it has been found that in the production of a (meth)acrylate, when more than 3 by mass of a reaction product of an alcohol and a fatty acid anhydride, a (meth)acrylate, and the alcohol are mixed in recovered (meth)acrylic acid, the purity of a (meth)acrylate produced using the recovered (meth)acrylic acid decreases largely. In addition, as a result of further study, it has been found that the reaction product of an alcohol and a fatty acid anhydride, the (meth)acrylate, and the alcohol contained in the recovered (meth)acrylic acid react with a fatty acid, produced as a by-product in the step of producing (meth)acrylic anhydride, to change to a fatty acid alcohol ester. It has turned out that this fatty acid alcohol ester remains until the step of producing a (meth)acrylate, and the removal of the fatty acid alcohol ester by a purification operation, such as distillation, is difficult, thereby causing a decrease in purity.

CITATION LIST

Patent Literature

Patent Literature 1: JP2000-191590A
Patent Literature 2: JP2003-40832A
Patent Literature 3: JP54-135706A

SUMMARY OF INVENTION

Technical Problem

It is an object of the present invention to provide a method for producing (meth)acrylic anhydride with high yield and high purity in a method for reacting (meth)acrylic acid with a fatty acid anhydride to produce (meth)acrylic anhydride. It is another object of the present invention provide method for storing (meth)acrylic anhydride that suppresses the decrease of the (meth)acrylic anhydride over time.

It is a further object of the present invention to provide a method for producing a (meth)acrylate with high purity, effectively using (meth)acrylic acid produced as a by-product, in a method for reacting (meth)acrylic acid with a fatty acid anhydride to produce (meth)acrylic anhydride, and reacting the produced (meth)acrylic anhydride with an alcohol to produce a (meth)acrylate.

Solution to Problems

The present inventors have found that when 0.3 times moles or more of (meth)acrylic acid coexists with respect to (meth)acrylic anhydride, the stability of the (meth)acrylic anhydride is improved significantly. In addition, the present inventors have found that the stability is improved by using a particular catalyst.

Specifically, a first aspect of the present invention is
a method for producing (meth)acrylic anhydride, including reacting a fatty acid anhydride represented by the following general formula (1) with (meth)acrylic acid to produce (meth)acrylic anhydride, while extracting a fatty acid produced as a by-product, wherein
the reaction is performed, while adjustment is performed so that a molar ratio of the (meth)acrylic acid to the (meth)acrylic anhydride in a reaction liquid is 0.3 or more,

[Formula 1]

(1)

wherein $R^1$ represents a linear or branched alkyl group or alkenyl group having 1 to 3 carbon atoms, and $R^2$ represents a linear or branched alkyl group having 1 to 3 carbon atoms.

In addition, a second aspect of the present invention is
a method for producing (meth)acrylic anhydride, including reacting a fatty acid anhydride represented by the following general formula (1) with (meth)acrylic acid to produce (meth)acrylic anhydride, while extracting a fatty acid produced as a by-product, wherein
the reaction is performed in the presence of a catalyst composed of a compound containing a metal having a Pauling electronegativity of 1.0 or more,

[Formula 2]

(1)

wherein $R^1$ represents a linear or branched alkyl group or alkenyl group having 1 to 3 carbon atoms, and $R^2$ represents a linear or branched alkyl group having 1 to 3 carbon atoms.

In addition, a third aspect of the present invention is
a method for storing (meth)acrylic anhydride, including allowing (meth)acrylic acid to coexist in an amount of 0.3 to 2 moles with respect to 1 mole of (meth)acrylic anhydride.

Further, it has been found that in producing a (meth)acrylate using the (meth)acrylic anhydride obtained according to the first aspect or the second aspect of the present invention, when the total content of a reaction product of an alcohol and the fatty acid anhydride represented by the general formula (1), a (meth)acrylate, and the alcohol in recovered (meth)acrylic acid is less than 3% by mass, a decrease in the purity of a (meth)acrylate produced using the recovered (meth) acrylic acid is suppressed.

Specifically, a fourth aspect of the present invention is
a method for producing a (meth)acrylate, including the following series of step (A) to step (C):
(A) a step of producing (meth)acrylic anhydride according to the first aspect or the second aspect;
(B) a step of reacting an alcohol with the (meth)acrylic anhydride obtained in the reaction in the step (A) to produce a (meth)acrylate; and
(C) a step of purifying the unpurified (meth)acrylate obtained in the step (B) to obtain the (meth)acrylate, including the following step (C1) and step (C2):
(C1) a step of recovering (meth)acrylic acid produced as a by-product in the reaction in the step (B) by distillation so that a total content of a reaction product of the alcohol and the fatty acid anhydride represented by the general formula (1), produced as a by-product in the reaction in the step (B), the (meth)acrylate, and the alcohol is 3% or less by mass in a distillate; and
(C2) a step of purifying the reaction liquid that is not distilled in the step (C1) to obtain the (meth)acrylate, wherein
when they series of they step (A) to the step (C) is performed to produce the (meth)acrylate, and then a next series of the step (A) to the step (C) is performed, the (meth)acrylic acid recovered in the step (C1) in the previous series of steps is used in the step (A).

Advantageous Effects of Invention

According to the method for producing (meth)acrylic anhydride according to the present invention, (meth)acrylic anhydride can be obtained with high yield and high purity. In addition, the method for storing (meth)acrylic anhydride according to the present invention suppresses the decrease of the (meth)acrylic anhydride over time and provides high storage stability.

According to the method of the present invention, it is possible to obtain a (meth)acrylate with high purity, effectively using (meth)acrylic acid produced as a by-product, in a method for reacting (meth)acrylic acid with a fatty acid anhydride to produce (meth)acrylic anhydride, and reacting the produced (meth)acrylic anhydride with an alcohol to produce a (meth)acrylate.

DESCRIPTION OF EMBODIMENTS

In the present invention, (meth)acrylic acid represents acrylic acid or methacrylic acid, and (meth)acrylic anhydride represents acrylic anhydride, methacrylic anhydride, or an acid anhydride of acrylic acid and methacrylic acid (mixed anhydride). In addition, phenyl(meth)acrylate represents phenyl methacrylate or phenyl acrylate, and a (meth)acrylate represents an acrylate or a methacrylate. In the present invention, (meth)acrylic anhydride is produced by the method of the following step (A).

In addition, in the present invention, a (meth)acrylate is produced by a method including the following step (A) to step (C). In the present invention, when a series of the step (A) to the step (C) is performed to produce a (meth)acrylate, and then the next series of the step (A) to the step (C) is performed, (meth)acrylic acid recovered in a step (C1) in the previous series of steps can be used in the step (A).

(A) The step of producing (meth)acrylic anhydride;
(B) the step of reacting an alcohol with the (meth)acrylic anhydride obtained in the reaction in the above step (A) to produce a (meth)acrylate; and
(C) the step of purifying the unpurified (meth)acrylate obtained in the above step (B) to obtain the (meth)acrylate, including the following step (C1) and step (C2):

(C1) the step of recovering (meth)acrylic acid produced as a by-product in the reaction in the above step (B) by distillation so that the total content of a reaction product of the above alcohol and a fatty acid anhydride represented by the general formula (1), produced as a by-product in the reaction in the above step (B), the (meth)acrylate, and the above alcohol is 3% or less by mass in the distillate; and (C2) the step of purifying the reaction liquid that is not distilled in the above step (C1) to obtain the (meth)acrylate.

[Step (A): The Step of Producing (Meth)Acrylic Anhydride]

The step of reacting a fatty acid anhydride represented by the above general formula (1) with (meth)acrylic acid to produce (meth)acrylic anhydride, while extracting a fatty acid produced as a by-product, will be described.

The method for producing (meth)acrylic anhydride according to the present invention is a method for producing (meth)acrylic anhydride, including reacting a fatty acid anhydride represented by the above general formula (1) with (meth)acrylic acid to produce (meth)acrylic anhydride, while extracting a fatty acid produced as a by-product, wherein the reaction is performed, while adjustment is performed so that the molar ratio of the (meth)acrylic acid to 1 mole of the (meth)acrylic anhydride in the reaction liquid is 0.3 or more.

In addition, the method for producing (meth)acrylic anhydride according to the present invention is a method for producing (meth)acrylic anhydride, including reacting a fatty acid anhydride represented by the above general formula (1) with (meth)acrylic acid to produce (meth)acrylic anhydride, while extracting a fatty acid produced as a by-product, wherein the reaction is performed in the presence of a catalyst comprising a compound comprising a metal having a Pauling electronegativity of 1.0 or more.

In the method for producing (meth)acrylic anhydride in this step, the fatty acid anhydride used as a raw material is a compound represented by the above general formula (1).

Specifically, examples of $R^1$ include a methyl group, an ethyl group, a propyl group, an isopropyl group, a vinyl group, an allyl group, and an isopropenyl group. Examples of $R^2$ include a methyl group, an ethyl group, a propyl group, and an isopropyl group. For $R^1$, a methyl group, an ethyl group, and a vinyl group are preferred, and a methyl group is more preferred, in terms of the separability of the fatty acid, produced as a by-product by the reaction with the (meth)acrylic acid, from the produced (meth)acrylic anhydride in the distillation column. Similarly, for $R^2$, a methyl group and an ethyl group are preferred, and a methyl group is more preferred. Acetic anhydride (an acid anhydride of acetic acids) is preferred as the fatty acid anhydride, in terms of the above reason and the safety of the fatty acid produced as a by-product by the reaction.

In the production method in this step, the above fatty acid anhydride is reacted with (meth)acrylic acid. The fatty acid produced as a by-product at this time is the same as a fatty acid produced by the hydrolysis of the fatty acid anhydride. For example, when the fatty acid anhydride is acetic anhydride, the fatty acid produced as a by-product is acetic acid.

In addition, when the (meth)acrylic anhydride is produced, a mixed anhydride of the fatty acid derived from the fatty acid anhydride and the (meth)acrylic acid (hereinafter referred to as a mixed anhydride) is present as an intermediate.

When in the above general formula (1), $R^1$ is a group other than a vinyl group derived from acrylic acid reacted, or an isopropenyl group derived from methacrylic acid, a mixed anhydride is produced. For example, in the reaction of acetic anhydride with acrylic acid, a mixed anhydride in which in the general formula (1), $R^1$ is a vinyl group, and $R^2$ is a methyl group is produced. Therefore, these mixed anhydrides can further react with the (meth)acrylic acid.

In the present invention, the molar ratio of the (meth)acrylic acid to the (meth)acrylic anhydride in the reaction liquid is adjusted to 0.3 or more. By setting the above molar ratio to 0.3 or more, the stability of the (meth)acrylic acid is improved. As this molar ratio increases, the stability of the (meth)acrylic anhydride is more improved. Therefore, the above molar ratio is preferably 0.5 or more.

In the present invention, the molar ratio of the (meth)acrylic acid to the (meth)acrylic anhydride in the reaction liquid is preferably adjusted to 0.3 to 2 at the completion of the reaction. For a reason similar to the above, the molar ratio is more preferably 0.5 or more. On the other hand, for the reason that as the amount of the methacrylic acid with respect to the amount of the (meth)acrylic anhydride increases, the size of the reactor increases when a (meth)acrylate is produced using the obtained reaction liquid, and a container with a large volume becomes necessary during storage, and the load for separating the obtained (meth)acrylate from the (meth)acrylic acid increases, as described later, and so on, the above molar ratio is preferably 2 or less. The above molar ratio is more preferably 1 or less, and further preferably 0.8 or less. As the molar ratio of the (meth)acrylic acid to the (meth) acrylic anhydride increases, an increase in the effect of the present invention with respect to an increase in molar ratio decreases. Therefore, priority may be given to the solution of the above problem.

Even if the molar ratio of the (meth)acrylic acid to the (meth)acrylic anhydride is temporarily out of the above range during the process of the reaction, it is not a problem if it is a short time.

In this step, preferably, the point when the molar ratio of the fatty acid anhydride, a raw material, to the (meth)acrylic anhydride, the product, is 0.01 or less is taken as the time of the completion of the reaction.

But, even if the amount of the fatty acid anhydride is equal to or less than the detection limit, the mixed anhydride remains, and therefore, the reaction is more preferably completed, with the molar ratio of the amount of the mixed anhydride to the amount of the (meth)acrylic anhydride being 0.02 or less. For example, if a mixed anhydride of acetic acid and (meth)acrylic acid is present in (meth)acrylic anhydride, an acetate and (meth)acrylic acid are produced when the (meth)acrylic anhydride is reacted with an alcohol, and therefore, the yield and selectivity of the target (meth)acrylate decrease. In terms of the yield of the (meth)acrylic anhydride, and the yield and selectivity in producing a (meth)acrylate, the reaction is further preferably completed, with the molar ratio of the mixed anhydride to the (meth)acrylic anhydride being 0.01 or less, and the reaction is particularly preferably completed, with the molar ratio being 0.005 or less. In addition, the reaction is preferably completed, with the molar ratio of the mixed anhydride to the (meth)acrylic anhydride being 0.0001 or more, and the reaction is more preferably completed, with the molar ratio being 0.001 or more, because a longer reaction time leads to an increase in by-products.

Examples of the method of adjusting the molar ratio of the (meth)acrylic acid to the (meth)acrylic anhydride in the reaction liquid to be 0.3 or more, and the method of performing adjustment so that the above molar ratio is 0.3 to 2 at the completion of the reaction include a method of determining the feed amount, considering the specifications and ability of the apparatus, a method of analyzing the composition of the reaction liquid or the distillate, calculating the amount of the (meth)acrylic acid or the fatty acid anhydride additionally supplied, and supplying it, and a method of analyzing the composition of the reaction liquid or the distillate, determining operation conditions, such as temperature, pressure, and reflux ratio, and controlling them.

Among these methods, the method of additionally supplying the (meth)acrylic acid or the fatty acid anhydride is preferred because of easy controllability, and a method of supplying the (meth)acrylic acid during the entire period or the latter stage of the reaction is preferred. The supply method may be any method, such as a method of directly introducing the (meth)acrylic acid or the fatty acid anhydride into the reaction container, or a method of supplying the (meth)acrylic acid or the fatty acid anhydride by introducing it into the distillation column and allowing it to descend in the column.

Examples of the method of calculating the amount of the methacrylic acid or the fatty acid anhydride additionally supplied include a method of first increasing the feed molar ratio of the (meth)acrylic acid to the fatty acid anhydride by about four times, periodically analyzing the composition in the still when extracting the fraction, while appropriately increasing the reflux ratio from 1.5 in a rectifying column having a theoretical plate number of 10, and additionally supplying the fatty acid anhydride so as to provide the target molar ratio, and a method of first increasing the feed molar ratio of the (meth)acrylic acid to the fatty acid anhydride by about two times, periodically analyzing the composition in the still when extracting the fraction, while appropriately increasing the reflux ratio from 2 in a rectifying column having a theoretical plate number of 10, and additionally supplying the (meth)acrylic acid in such an amount that the fatty acid anhydride and the mixed anhydride disappear.

In related art, when a fatty acid anhydride is reacted with (meth)acrylic acid, while a fatty acid produced as a by-product is extracted, the amount of (meth)acrylic anhydride produced is small, and the molar ratio of the (meth)acrylic acid to the (meth)acrylic anhydride is large, in the first half of the reaction, and therefore, the (meth)acrylic anhydride is relatively stable. But, with the progress of the reaction, the (meth)acrylic acid is consumed, and in addition, part of the (meth)acrylic acid is distilled, together with the fatty acid produced as a by-product, and therefore, the molar ratio of the (meth)acrylic acid to the (meth)acrylic anhydride decreases. Therefore, in the related art, at the latter stage of the reaction, little (meth)acrylic acid remains, and the stability of the produced (meth)acrylic anhydride decreases largely.

In the production of (meth)acrylic anhydride, 2 to 8 times moles of (meth)acrylic acid, a raw material, is preferably used with respect to a fatty acid anhydride. In terms of the yield of the (meth)acrylic anhydride based on the fatty acid anhydride, the (meth)acrylic acid is preferably 2.2 times moles or more, and more preferably 2.4 times moles or more, with respect to the fatty acid anhydride.

In addition, in terms of reducing the load of adjusting the amount of the (meth)acrylic acid in setting the molar ratio of the (meth)acrylic acid to the (meth)acrylic anhydride in the reaction liquid to 0.3 to 2 at the completion of the reaction, the (meth)acrylic acid is preferably 6 times moles or less, and more preferably 4 times moles or less, with respect to the fatty acid anhydride.

The method of first feeding the raw materials to the reactor may be any of a method of feeding both of the fatty acid anhydride and the (meth)acrylic acid together, a method of feeding either one raw material to the reactor, a method of feeding all of one raw material and feeding part of the other, or a method of feeding part of both raw materials. In the cases of the latter three, the remaining raw material may be supplied by either method of division or continuation after the start of the reaction.

In addition, in the method for producing (meth)acrylic anhydride in this step, a catalyst can be used. Without a catalyst, the reaction time is long, and undesirable side reaction products due to the degradation reaction of the (meth)acrylic anhydride, multimerization of the (meth)acrylic anhydride, the Michael addition of the methacrylic acid, and the like increase.

Examples of the catalyst include metal compounds, acid catalysts, base catalysts, and heterogeneous catalysts.

Examples of the above metal compounds include metal oxides, hydroxides, salts of metals and inorganic acids, such as carbonates, hydrogencarbonates, sulfates, chlorides, nitrates, phosphates, and borates; organic acid salts, such as acetates, (meth)acrylates, and sulfonates; and complex salts, such as acetylacetonate and cyclopentadienyl complexes.

Examples of the above acid catalysts include inorganic acids, such as sulfuric acid, nitric acid, phosphoric acid, boric acid, hydrochloric acid, and heteropolyacid; and organic acids, such as metanesulfonic acid, para-toluenesulfonic acid, and camphorsulfonic acid. In addition, examples of the base catalysts include organic bases, such as pyridine, 4-(dimethylamino)pyridine, and triethylamine.

Ion exchange resins, such as basic ion exchange resins and acidic ion exchange resins, and catalysts in which an active component is fixed to a carrier, such as silica, alumina, or titania, can be used as the above heterogeneous catalysts.

Among the above catalysts, metal compounds are preferred in terms of activity (reaction speed), selectivity, and the prevention of coloration. Compounds of metals having a Pauling electronegativity of 1.0 or more are preferred, and compounds of metals having a Pauling electronegativity of 1.5 or more are more preferred, because of a small amount of side reaction products Compounds of one or more metals selected from vanadium, manganese, iron, cobalt, nickel, copper, zinc, zirconium, and indium are further preferred. Particularly, compounds of cobalt, nickel, or indium are optimum because of a small amount of undesirable by-products. In terms of activity, those belonging to the second period to the fifth period of the periodic table are preferred, those belonging to the fourth period to the fifth period are more preferred, and compounds of vanadium, manganese, cobalt, nickel, zirconium, zinc, or indium are more preferred. In addition, in terms of selectivity, oxides, hydroxides, salts, such as carbonates, acetates, and (meth)acrylates, are preferred for the metal compounds.

Among the above catalysts, compounds of cobalt, nickel, or indium are most preferred in terms of activity and selectivity.

On the other hand, compounds of metals, such as sodium, potassium, rubidium, and cesium, which are metals having a Pauling electronegativity of less than 1.0, are undesirable.

In addition, for the above catalyst, one the total required amount of which is dissolved in the reaction system is preferred in terms of operability. The catalyst may be used alone, or two or more catalysts may be used in combination. As long as the function of the catalyst of the present invention is not impaired, the catalyst may contain other elements or compounds.

Examples of the method of feeding the catalyst to the reactor include a method of first feeding a total amount to the reactor, and a method of first feeding a part and supplying the remainder later.

The amount of the above catalyst used is preferably 0.000001 to 0.005 times moles, with respect to the total feed amount of the fatty acid anhydride represented by the above general formula (1), used throughout the entire reaction. In terms of allowing the reaction to proceed smoothly, the amount of the catalyst used is preferably 0.000005 times moles or more, and more preferably 0.00001 times moles or more, with respect to the feed amount of the fatty acid anhydride represented by the above general formula (1). On the other hand, in terms of the removal of the catalyst, and the suppression of side reactions, the amount of the catalyst used is preferably 0.001 times moles or less, and more preferably 0.0005 times moles or less, with respect to the feed amount of the fatty acid anhydride represented by the above general formula (1). Particularly, 0.0001 times moles or less is further preferred because there is no loss of the fatty acid anhydride, and even unpurified (meth)acrylic anhydride can be sufficiently used for an esterification reaction and the like.

The reaction is preferably performed without a solvent, in terms of productivity, the load of solvent recovery, and the like, but a solvent inert to the reaction can also be used as required. For example, aliphatic hydrocarbons, such as hexane, heptane, pentane, and cyclohexane; aromatic hydrocarbons, such as toluene and xylene; ether-based solvents, such as diethyl ether and diisopropyl ether; and ketone-based solvents, such as diethyl ketone and diisopropyl ketone, can be used as the inert solvent. When the inert solvent is used, the amount of the inert solvent used is preferably an amount 1 to 30 times the mass of the (meth)acrylic acid. As the solvent, those easily undergoing azeotropy with the fatty acid produced as a by-product are preferred.

The reaction temperature for producing the (meth)acrylic anhydride is preferably in the range of 30 to 120° C. The reaction temperature is more preferably 50° C. or more, and further preferably 60° C. or more, in that the reaction can be allowed to proceed smoothly. On the other hand, the reaction temperature is more preferably 100° C. or less, and further preferably 90° C. or less, in terms of suppressing polymerization and side reactions.

Examples of the reaction scheme include a batch type in which all raw materials are fed into a single reactor to complete the reaction, a continuous type in which the raw materials are continuously supplied into a reactor and continuously reacted, and a circulation type including a reactor and a mixing tank in which the raw materials are reacted in the reactor, while being circulated between the reactor and the mixing tank. In order to remove compounds having a lower boiling point than the (meth)acrylic anhydride, such as the fatty acid produced as a by-product, as much as possible, a batch type is preferred.

The reaction is performed, while the fatty acid produced as a by-product is removed out of the system. Examples of the method of separating the fatty acid produced as a by-product from other compounds include a method of performing distillation using a distillation column (rectifying column) having a plurality of plates. For example, packed columns using a packing having the shape of a Raschig ring, a Lessing ring, a Dixon packing, a Pall ring, a saddle, a Sulzer packing, or the like, made of stainless steel, glass, ceramic, or the like, plate columns, such as a porous plate column and a bubble cap column, and the like can be used for the distillation column. The connection of the distillation column and the reactor may be any of a form in which the distillation column is connected to the upper portion of the reactor, a form in which the distillation column is connected to the upper portion of another container connected to the reactor, and a form in which the reactor is connected to any position from the upper plate to the lower plate of the distillation column. In all connection forms, the number of paths between the reactor and the distillation column may be one or plural, and an apparatus, such as a heat exchanger, may be interposed in midstream.

The theoretical plate number of the distillation column is preferably 3 or more, and more preferably 5 or more, in terms of the separability of the fatty acid produced as a by-product from other compounds. On the other hand, the theoretical plate number of the distillation column is preferably 30 or less, and more preferably 20 or less, in terms of differential pressure and apparatus scale.

The theoretical plate number of the distillation column is preferably 3 or more, and more preferably 5 or more, in terms of the separability of the fatty acid produced as a by-product from other compounds. On the other hand, the theoretical plate number of the distillation column is preferably 30 or less, and more preferably 20 or less, in terms of differential pressure and apparatus scale.

In the distillation, internal reflux using no reflux apparatus, or a scheme using a reflux apparatus to control the reflux ratio can be used. The reflux ratio can be appropriately determined, considering the scale of the apparatus, productivity, separability, and the like, and is preferably in the range of 0.2 to 10. The reflux ratio is more preferably 0.5 or more, and further preferably 1 or more, in terms of separability. On the other hand, the reflux ratio is more preferably 6 or less, and further preferably 4 or less, in terms of productivity. The reflux ratio is preferably appropriately adjusted during the reaction, according to the composition of the reaction liquid.

When the fatty acid produced as a by-product is removed out of the system, it is not necessary to completely separate the fatty acid from other compounds. In addition, when the fatty acid anhydride, the mixed anhydride, and the (meth)acrylic anhydride are distilled, together with the fatty acid, from the distillation column, part or all of the distillate may be used for the production of another (meth)acrylic anhydride.

The pressure can be appropriately determined, considering the reaction temperature, the plate number of the distillation column, and the like. With the progress of the reaction, the composition of the reaction liquid changes, and the vapor pressure of the whole decreases. Therefore, in order to remove the fatty acid produced as a by-product, it is preferred to lower the pressure so that rectification can be carried out. The reaction is carried out, while the pressure in the still is adjusted. But, the pressure of the column top may be adjusted, considering the reaction temperature, the plate number of the distillation column, and the like. Examples of such a method include a method of adjusting the reaction temperature to 80° C. at atmospheric pressure to start the reaction, and then gradually reducing the pressure.

The reaction time in this step can be appropriately determined, based on the amount of the fatty acid anhydride represented by the general formula (1) or the mixed anhydride remaining in the reaction container. But, a problem is that in order to complete the reaction in less than 12 hours, the equipment, such as the rectifying column, is too large, with respect to the amount of the (meth)acrylic anhydride produced. Therefore, the reaction time is preferably 12 hours or more. In terms of the yield of the (meth)acrylic anhydride, and the size of the rectifying column equipment, the reaction time is preferably 15 hours or more, and more preferably 18 hours or more. On the other hand, in terms of productivity, the reaction time is preferably 72 hours or less, more preferably 60 hours or less, and further preferably 48 hours or less. In addition, as the reaction time decreases, side reactions are more suppressed. The reaction time is defined as the time from the point of the start of reaction, when the removal of the fatty acid is started in a batch type or a half-batch type reaction apparatus, to the time of the completion of the above reaction. The completion of the reaction is carried out by stopping the removal of the fatty acid or the remaining (meth)acrylic acid. The reaction time in the case of a continuous type is the time required to produce the same amount of the (meth)acrylic anhydride as the actual volume of the reaction container.

In this step, a polymerization inhibitor can be used in the production of the (meth)acrylic anhydride. The polymerization inhibitor is introduced into the reactor, and preferably, the polymerization inhibitor is also introduced into the column top of the distillation column and in the midstream of the column. For the polymerization inhibitor used in the reactor, polymerization inhibitors inert to the acid anhydride and the (meth)acrylic acid are preferred.

Examples of the polymerization inhibitor include quinone-based polymerization inhibitors, such as hydroquinone, hydroquinone monomethyl ether, and benzoquinone, alkylphenol-based polymerization inhibitors, such as 2,6-di-tert-butylphenol, 2,4-di-tert-butylphenol, 2-tert-butyl-4,6-dimethylphenol, 2,6-di-tert-butyl-4-methylphenol, and 2,4,6-tri-tert-butylphenol, amine-based polymerization inhibitors, such as alkylated diphenylamine, N,N'-diphenyl-p-phenylenediamine, and phenothiazine, hindered amine-based polymerization inhibitors, such as 4-hydroxy-2,2,6,6-tetramethylpiperidine-N-oxyl, 4-benzoyloxy-2,2,6,6-tetramethylpiperidine-N-oxyl, and 4-acetamino-2,2,6,6-tetramethylpiperidine-N-oxyl, and copper dithiocarbamate-based polymerization inhibitors, such as metal copper, copper sulfate, copper dimethyldithiocarbamate, copper diethyldithiocarbamate, and copper dibutyldithiocarbamate. One of these polymerization inhibitors may be used alone, or two or more of these polymerization inhibitors may be used in combination.

The amount of the polymerization inhibitor added is affected by its type and conditions, but is preferably in the range of 0.01 to 10000 ppm with respect to the weight of the reaction liquid. In addition, the effect of preventing polymerization may be improved by bubbling a gas containing oxygen in the reaction liquid.

The (meth)acrylic anhydride obtained by the production method in this step can be sufficiently used without being particularly subjected to purification treatment, because the (meth)acrylic anhydride, as it is, contains a small amount of impurities, other than the (meth)acrylic acid. However, when it is desired to obtain (meth)acrylic anhydride with higher purity, purification can be performed by a known method, such as rectification or washing, after the completion of the reaction. However, preferably, purification is not performed because the (meth)acrylic anhydride degrades during subsequent storage, as described later.

[Step (B): The Step of Reacting an Alcohol with the (Meth)acrylic Anhydride Obtained in the Reaction in the Above Step (A) to Produce a (Meth)acrylate]

The step of reacting an alcohol with the (meth)acrylic anhydride obtained in the reaction in the above step (A) to produce a (meth)acrylate, in the step (B), will be described.

Examples of the alcohol, a raw material, include straight-chain or branched-chain aliphatic alcohols, such as methyl alcohol, ethyl alcohol, n-propyl alcohol, isopropyl alcohol, n-butyl alcohol, sec-butyl alcohol, tert-butyl alcohol, isobutyl alcohol, n-amyl alcohol, isoamyl alcohol, n-hexyl alcohol, n-heptyl alcohol, n-octyl alcohol, n-nonyl alcohol, n-decyl alcohol, lauryl alcohol, cetyl alcohol, and stearyl alcohol, unsaturated alcohols, such as allyl alcohol and butynediol, cyclic alcohols, such as cyclopentanol, cyclohexanol, 1-adamantanol, 2-adamantanol, and 1-adamantanemethanol, aromatic alcohols, such as phenol and benzyl alcohol, and polyhydric alcohols, such as ethylene glycol, 1,2-propanediol, 1,3-propanediol, 1,2-butanediol, 1,3-butanediol, 1,4-butanediol, and glycerin, and further, these alcohols having a substituent, such as an amino group, a carboxyl group, a carbonyl group, or an amide group, at at least one position thereof, and alcohols having an ether bond, an ester bond, or the like in the structure. Among these alcohols, alcohols having 5 or more carbon atoms are preferred in terms of separability when the produced (meth)acrylate and (meth)acrylic acid are produced by distillation. In addition, alcohols not having a substituent reactive with the (meth)acrylic anhydride, such as an amino group, are preferred in terms of selectivity.

When the (meth)acrylate is produced in this step, 0.5 to 5 times moles of the (meth)acrylic anhydride is preferably used with respect to the alcohol. In terms of the yield of the (meth)acrylate based on the alcohol, and a reduction in the amount of the alcohol remaining, the (meth)acrylic anhydride is more preferably 0.8 times moles or more, and further preferably 0.9 times moles or more, with respect to the alcohol.

In addition, in terms of reducing the load of the treatment or recovery of the (meth)acrylic anhydride after the reaction, the (meth)acrylic anhydride is more preferably 1.2 times moles or less, and further preferably 1.1 times moles or less, with respect to the alcohol.

When the separation of the remaining (meth)acrylic anhydride from the (meth)acrylate by distillation is difficult, it is preferred to feed an excess amount of the alcohol with respect to the (meth)acrylic anhydride, in terms of the purity of the obtained (meth)acrylate.

The method of feeding the raw materials to the reactor may be any of 1) a method of feeding both of the (meth)acrylic anhydride and the alcohol together, 2) a method of feeding all of either one raw material to the reactor and then supplying the other raw material, 3) a method of feeding a total amount of one raw material and part of the other raw material and then supplying the remaining raw material, or 4) a method of feeding part of both raw materials and then supplying the remaining raw materials. When the raw material is supplied later, the remaining raw material may be supplied by any method, such as divided or continuous supply, after the start of the reaction.

In the production of the (meth)acrylate in this step, a catalyst is preferably used. Without a catalyst, the reaction time is long, and polymerization and side reactions may proceed.

Examples of the above catalyst include metal compounds, acid catalysts, base catalysts, and heterogeneous catalysts.

Examples of the above metal compounds include metal oxides, hydroxides, salts of metals and inorganic acids, such as carbonates, hydrogencarbonates, sulfates, chlorides, nitrates, phosphates, and borates; organic acid salts, such as acetates, (meth)acrylates, and sulfonates; and complex salts, such as acetylacetonates and cyclopentadienyl complexes.

Examples of the above acid catalysts include inorganic acids, such as sulfuric acid, nitric acid, phosphoric acid, boric acid, hydrochloric acid, and heteropolyacid; and organic acids, such as metanesulfonic acid, para-toluenesulfonic acid, and camphorsulfonic acid. In addition, examples of the above base catalysts include organic bases, such as pyridine, 4-(dimethylamino)pyridine, and triethylamine.

Ion exchange resins, such as basic ion exchange resins and acidic ion exchange resins, and catalysts in which an active component is fixed to a carrier, such as silica, alumina, or titania, can be used as the above heterogeneous catalysts.

Among these catalysts, acidic ion exchange resins, heteropolyacid, and the like are preferred in terms of activity. In addition, sulfuric acid-based catalysts, such as sulfuric acid, methanesulfonic acid, and para-toluenesulfonic acid, are preferred, and sulfuric acid is more preferred, in terms of the recovery rate of the (meth)acrylic acid.

The catalyst may be the same as or different from the one used in the step (A). In addition, for the catalyst, further, the same one or another one may be newly added to the one used in the step (A). The catalyst used in the step (A) may remain if this step is not adversely affected.

The above catalyst may be used alone, or two or more of the above catalysts may be used in combination. Examples of the method of feeding the above catalyst include a method of first feeding a total amount to the reactor, and a method of first feeding a part and supplying the remainder later.

In this step, the amount of the catalyst used is preferably 0.0001 to 0.3 times moles, with respect to the feed amount of the alcohol. In terms of allowing the reaction to proceed smoothly, the amount of the catalyst used is more preferably 0.001 times moles or more, and further preferably 0.01 times moles or more, with respect to the alcohol. On the other hand, in terms of the removal of the catalyst, and the suppression of side reactions, the amount of the catalyst used is more preferably 0.2 times moles or less, and further preferably 0.1 times moles or less, with respect to the alcohol.

The reaction is preferably performed without a solvent, in terms of productivity, the load of solvent recovery, and the like, but a solvent inert to the reaction can also be used as required. For example, aliphatic hydrocarbons, such as hexane, heptane, pentane, and cyclohexane; aromatic hydrocarbons, such as toluene and xylene; ethers, such as diethyl ether and diisopropyl ether; and ketones, such as diethyl ketone and diisopropyl ketone, can be used as such a solvent. For the solvent, those easily undergoing azeotropy with the fatty acid produced as a by-product are preferred. The amount of the solvent used is preferably 0.1 to 30 times the mass of the (meth)acrylic acid.

The reaction temperature for producing the (meth)acrylate is preferably in the range of 30 to 120° C. In terms of allowing the reaction to proceed smoothly, the reaction temperature is more preferably 50° C. or more, and further preferably 60° C. or more. On the other hand, in terms of suppressing polymerization and side reactions, the reaction temperature is more preferably 100° C. or less, and further preferably 90° C. or less.

Examples of the reaction scheme include a batch type in which all raw materials are fed into a single reactor to complete the reaction, a continuous type in which the raw materials are continuously supplied into a reactor and continuously reacted, and a circulation type including a reactor and a mixing tank in which the raw materials are reacted in the reactor, while being circulated between the reactor and the mixing tank. The reaction may be performed, while the (meth)acrylic acid produced as a by-product is recovered. The pressure may be any of a state in which the pressure is reduced, atmospheric pressure, and a state in which pressure is applied.

The reaction time in producing the (meth)acrylate can be appropriately determined, based on the amount of the (meth)acrylic anhydride or the alcohol remaining in the reaction container. Usually, the reaction is completed, with the molar ratio of the alcohol to the (meth)acrylate being 0.05 or less. In terms of decreasing the alcohol content in the recovered (meth)acrylic acid, the reaction is preferably completed, with the molar ratio of the alcohol to the (meth)acrylate being 0.03 or less, and the reaction is more preferably completed, with the molar ratio being 0.01 or less.

The reaction time can be appropriately determined from the feed ratio and the reaction temperature, but is usually 0.5 to 48. In terms of yield, the reaction time is preferably 1 hour or more, and more preferably 2 hours or more.

In terms of the suppression of polymerization and side reactions, the reaction time is preferably 36 hours or less, more preferably 24 hours or less, and further preferably 12 hours or less.

In the method for producing the (meth)acrylate, a polymerization inhibitor can be used. The polymerization inhibitor is introduced into the reactor, and preferably, the polymerization inhibitor is also introduced into the column top of the distillation column and in the midstream of the column. As the polymerization inhibitor used in the reactor, polymerization inhibitors inert to the acid anhydride and the (meth)acrylic acid are preferred.

Examples of the polymerization inhibitor that can be used include those similar to the polymerization inhibitors used in the step (A). One of these polymerization inhibitors may be used alone, or two or more of these polymerization inhibitors may be used in combination.

The amount of the polymerization inhibitor added is affected by its type and conditions, but is preferably in the range of 0.01 to 10000 ppm with respect to the mass of the reaction liquid. In addition, the effect of preventing polymerization may be improved by bubbling a gas containing oxygen in the reaction liquid.

[Step (C): The Step of Purifying the Unpurified (Meth)acrylate Obtained in the Above Step (B) to Obtain the (Meth)acrylate]

The step of purifying the (meth)acrylate obtained in the above step (B), which is produced as a by-product, to obtain the (meth)acrylate, in the step (C), will be described. The step (C) including the following step (C1) and step (C2).

Step (C1): the step of recovering (meth)acrylic acid produced as a by-product in the reaction in the above step (B) by distillation so that the total content of a reaction product of the above alcohol and a fatty acid anhydride represented by the above general formula (1), produced as a by-product in the reaction in the above step (B), the (meth)acrylate, and the above alcohol is 3% or less by mass in the distillate, and step (C2): the step of purifying the reaction liquid that is not distilled in the above step (C1) to obtain the (meth)acrylate.

In the step (C1), in the recovery of the (meth)acrylic acid, it is necessary to recover the (meth)acrylic acid by distillation so that the total content of the reaction product of the above alcohol and the fatty acid anhydride represented by the above general formula (1), produced as a by-product in the reaction in the above step (B), the (meth)acrylate, and the above alcohol, contained in the (meth)acrylic acid, is 3% or less by mass in the distillate. Hereinafter, "the total content of the reaction product of the above alcohol and the fatty acid anhydride represented by the above general formula (1), produced as a by-product in the reaction in the above step (B), the (meth) acrylate, and the above alcohol" is labeled as "the content of mixed substances".

If the content of the mixed substances contained in the recovered (meth)acrylic acid is high, a fatty acid ester, such as an acetate, is produced as a by-product in the step (A). The acetate produced as a by-product is stable, and therefore also remains in the subsequent step (B). An acetate often has a boiling point not largely different from that of a (meth)acrylate, and it is difficult to separate the acetate from the (meth) acrylate by purification, such as distillation. The production of the acetate as a by-product leads to a decrease in the purity of the (meth)acrylate. In addition, as the content of the acetate in the (meth)acrylate increases, the proportion of the acetate removed by purification decreases.

In terms of suppressing the decrease in the purity of the (meth)acrylate, the content of the mixed substances contained in the recovered (meth)acrylic acid is 3% or less by mass, and preferably 1% or less by mass. The content of the mixed substances is further preferably 0.5% or less by mass because the amount of the acetate in the (meth)acrylate produced reusing the (meth)acrylic acid recovered by the distillation can be reduced.

Examples of the method of reducing the content of the mixed substances include a method of adjusting the amount of the alcohol used with respect to the (meth)acrylic anhydride in the above-described range, and a method of appropriately adjusting distillation conditions, in the case of reducing the amount of the alcohol. Examples of the method of reducing the content of the mixed substances include a method of appropriately adjusting distillation conditions, in the case of reducing the amount of the (meth)acrylate or the reaction product of the alcohol and the fatty acid anhydride represented by the above general formula (1). Examples of the method of recovering the (meth)acrylic acid include simple distillation, and a method of performing distillation using a distillation column (rectifying column) having a plurality of plates. For example, packed columns using a packing having the shape of a Raschig ring, a Lessing ring, a Dixon packing, a Pall ring, a saddle, a Sulzer packing, or the like, made of stainless steel, glass, ceramic, or the like, plate columns, such as a porous plate column and a bubble cap column, and the like can be used for the distillation column. The distillation column may be any of the form of being connected to the upper portion of the reactor, the form of being connected to the upper portion of another container connected to the reactor by piping or the like, and a form in which connection is made from the reactor to any position from the upper plate to the lower plate of the distillation column by piping or the like. In all forms, the number of paths between the reactor and the distillation column may be one or plural, and an apparatus, such as a heat exchanger, may be interposed in midstream.

The theoretical plate number of the distillation column is preferably 3 or more, and more preferably 5 or more, in terms of reducing the content of the mixed substances contained in the (meth)acrylic acid. On the other hand, the theoretical plate number of the distillation column is preferably 30 or less, and more preferably 20 or less, in terms of differential pressure and apparatus scale.

In the distillation, internal reflux using no reflux apparatus, or a method using a reflux apparatus to control the reflux ratio can be used. The reflux ratio can be appropriately determined, considering the scale of the apparatus, productivity, separability, and the like, and is preferably in the range of 0.2 to 10. The reflux ratio is more preferably 0.5 or more, and further preferably 1 or more, in terms of reducing the content of the mixed substances contained in the (meth)acrylic acid. On the other hand, the reflux ratio is more preferably 6 or less, and further preferably 4 or less, in terms of productivity. The reflux ratio is preferably appropriately adjusted during the reaction, according to the composition of the reaction liquid.

The amount of the (meth)acrylic acid recovered is preferably 96% or less by mass, more preferably 94% or less by mass, and further preferably 92% or less by mass, with respect to the (meth)acrylic acid contained in the treated reaction liquid, in terms of reducing the content of the mixed substances contained in the (meth)acrylic acid. Subsequently distilled (meth)acrylic acid having a high content of the mixed substances may be introduced during the step of newly producing the (meth)acrylate, or the purification of the newly produced (meth)acrylate, and purified together.

The distillation temperature can be in the range of 10 to 150° C. In terms of sufficiently maintaining the amount of vapor, the distillation temperature is preferably 30° C. or more, and more preferably 50° C. or more. In terms of suppressing polymerization and side reactions, the distillation temperature is preferably 130° C. or less, and more preferably 110° C. or less.

The pressure can be appropriately determined, considering the temperature, the plate number of the distillation column, and the like. The distillation is preferably performed under reduced pressure, in that the distillation temperature can be lowered.

In the recovery of the (meth)acrylic acid, a polymerization inhibitor can be used. The polymerization inhibitor is introduced into the reactor, and preferably, the polymerization inhibitor is also introduced into the column top of the distillation column and in the midstream of the column. For the polymerization inhibitor used in the reactor, polymerization inhibitors inert to the (meth)acrylic acid are preferred.

Examples of the polymerization inhibitor that can be used include polymerization inhibitors similar to those in the step (A). One of these polymerization inhibitors may be used alone, or two or more of these polymerization inhibitors may be used in combination.

By appropriately setting the above conditions, the content of the mixed substances contained in the recovered (meth) acrylic acid can be 3% or less by mass.

In the step (C2), the (meth)acrylate can be purified by a known method, such as distillation, adsorbent treatment, washing, or crystallization, after the recovery of the (meth) acrylic acid.

Examples of the method of distilling the (meth)acrylate include methods, such as simple distillation, a distillation column (rectifying column) having a plurality of plates, and thin-film distillation. For example, packed columns using a packing having the shape of a Raschig ring, a Lessing ring, a Dixon packing, a Pall ring, a saddle, a Sulzer packing, or the like, made of stainless steel, glass, ceramic, or the like, plate columns, such as a porous plate column and a bubble cap column, and the like can be used for the distillation column. The distillation column may be any of the form of being connected to the upper portion of the reactor, the form of being connected to the upper portion of another container connected to the reactor by piping or the like, and a form in which connection is made from the reactor to any position from the upper plate to the lower plate of the distillation column by piping or the like. In all forms, the number of paths between the reactor and the distillation column may be one or plural, and an apparatus, such as a heat exchanger, may be interposed in midstream.

The theoretical plate number of the distillation column is preferably 3 or more, and more preferably 5 or more, in terms of the purity of the (meth)acrylate. On the other hand, the theoretical plate number of the distillation column is preferably 30 or less, and more preferably 20 or less, in terms of differential pressure and apparatus scale.

In the distillation, internal reflux using no reflux apparatus, or a method using a reflux apparatus to control the reflux ratio can be used. The reflux ratio can be appropriately determined, considering the scale of the apparatus, productivity, separability, and the like, and is preferably in the range of 0.2 to 10. The reflux ratio is more preferably 0.5 or more, and further preferably 1 or more, in terms of the purity of the (meth)acrylate. On the other hand, the reflux ratio is more preferably 6 or less, and further preferably 4 or less, in terms of productivity. The reflux ratio is preferably appropriately adjusted during the reaction, according to the composition of the reaction liquid.

The distillation temperature can be in the range of 10 to 180° C. In terms of sufficiently maintaining the amount of vapor, the distillation temperature is preferably 30° C. or more, and more preferably 50° C. or more. In terms of suppressing polymerization and side reactions, the distillation temperature is preferably 160° C. or less, and more preferably 140° C. or less.

The pressure can be appropriately determined, considering the temperature, the plate number of the distillation column, and the like. The distillation is preferably performed under reduced pressure, in that the distillation temperature can be lowered.

Examples of the method of washing the (meth)acrylate include a method of washing with water, an aqueous solution of a salt, such as common salt or sodium sulfate, or an aqueous solution of a basic substance. Examples of the basic substance include hydroxides of alkali metals, such as sodium hydroxide and potassium hydroxide; hydroxides of alkaline-earth metals, such as calcium hydroxide and magnesium hydroxide; carbonates of alkali metals, such as sodium carbonate and potassium carbonate; carbonates of alkaline-earth metals, such as calcium carbonate and magnesium carbonate; hydrogencarbonates of alkali metals, such as sodium hydrogencarbonate and potassium hydrogencarbonate; carbonates of alkaline-earth metals, such as calcium hydrogencarbonate and magnesium hydrogencarbonate; and organic bases, such as pyridine, 4-(dimethylamino)pyridine, and triethylamine. In addition, it is also possible to use two or more of these basic substances in combination. The washing may be performed once or a plurality of times. Further, it is also possible to perform washing a plurality of times with aqueous solutions of different basic substances. After washing with the basic substance, it is preferred to perform washing with water in order to remove the basic substance remaining in the organic layer. For the water used for the washing, distilled water, or pure water deionized with an ion exchange resin or the like is preferably used.

The concentration of the salt or the basic substance in the aqueous solution for washing is preferably 1 to 30% by mass, and more preferably 2 to 15% by mass. If the amount of the washing water is less than 1% by mass, the effect of washing is not sufficiently obtained. If the amount of the washing water is more than 30% by mass, a precipitate may be formed.

In order to increase the separability of the reaction liquid, an organic solvent may be added as required. As examples of the solvent that can be used, the same solvents as mentioned for the step (B) can be used.

The amount of the solvent is preferably 0.1 to 10 times, more preferably 0.5 to 5 times, that of the reaction liquid. If the amount of the solvent is less than 0.1 times, migration to the water or the aqueous solution used for the washing may occur. If the amount of the solvent is more than 10 times, it may take time to recover the solvent.

Examples of the method of treating the (meth)acrylate with an adsorbent include column chromatography, and a method of suspending an adsorbent to adsorb impurities, and then separating the adsorbent.

Examples of the adsorbent include activated clay, hydrotalcites, porous polymers, ion exchange resins (cation exchange resins or anion exchange resins), activated carbon, adsorption resins, silica gel, silica-alumina-based adsorbents, alumina gel, activated alumina, silicon dioxide, and zeolite.

The amount of the adsorbent used is 0.05 to 20% by mass with respect to the (meth)acrylate, and particularly, preferably 0.5 to 10% by mass. If the amount of the adsorbent used is less than 0.05% by mass, the effect of decreasing impurities is not sufficiently obtained. If the amount of the adsorbent used is more than 20% by mass, the loss due to the adsorption of the (meth)acrylate, and the load when the adsorbent is separated by filtration or the like are large.

The temperature when the (meth)acrylate is contacted with the adsorbent is not particularly limited, but is usually 0 to 100° C. In terms of the suppression of side reactions during the treatment, the temperature in the contact is preferably 60° C. or less, and more preferably 40° C. or less.

The time when the reaction liquid is contacted with the adsorbent is different according to the type of the adsorbent, the amount of the adsorbent used, and the like, but is usually about 1 to 120 minutes, and particularly, preferably about 3 to 60 minutes.

After the adsorption treatment with the adsorbent is performed, the (meth)acrylate can be separated from the adsorbent by a method, for example, filtration. Examples of the filter include membrane filters made of fluororesins, such as polytetrafluoroethylene.

An organic solvent may be added to the reaction liquid, as required. As examples of the solvent that can be used, the same solvents as mentioned for the step (B) can be used.

The amount of the solvent is preferably 0.1 to 10 times, more preferably 0.5 to 5 times, that of the reaction liquid. If the amount of the solvent is less than 0.1 times, migration to the water or the aqueous solution used for the washing may occur. If the amount of the solvent is more than 10 times, it takes time to recover the solvent.

Examples of the method of crystallizing the (meth)acrylate include a method of lowering the temperature of the reaction liquid to precipitate a crystal, and a method of removing the low-boiling substances in the reaction liquid for concentration to precipitate a crystal. When the crystallization is performed, a solvent may be added. For the solvent, saturated hydrocarbon solvents are preferred. Examples of the saturated hydrocarbon solvents include hexane, cyclohexane, methylcyclohexane, ethylcyclohexane, heptane, nonane, octane, isooctane, and decane. These may be one, or two or more of these may be mixed and used.

In the purification of the (meth)acrylate, a polymerization inhibitor can be used. The polymerization inhibitor is introduced into the reactor, and preferably, the polymerization inhibitor is also introduced into the column top of the distillation column and in the midstream of the column. For the polymerization inhibitor used in the reactor, polymerization inhibitors inert to the (meth)acrylate are preferred.

Examples of the polymerization inhibitor that can be used include polymerization inhibitors similar to those in the step (A). One of these polymerization inhibitors may be used alone, or two or more of these polymerization inhibitors may be used in combination.

[Use of Recovered (Meth)acrylic Acid]

In the present invention, when a series of the step (A) to the step (C) is performed to produce the (meth)acrylate, and then the next series of the step (A) to the step (C) is performed, the (meth)acrylic acid recovered in the step (C1) in the previous series of steps is used in the step (A).

A method of reusing the (meth)acrylic acid recovered in the step (C1) as the (meth)acrylic acid used in the above step (A) will be described.

The (meth)acrylic acid recovered in the above step (C1) has high purity, and therefore can be used as the (meth)acrylic acid used in the above step (A), as it is. But, washing, redistillation, treatment with an adsorbent, or the like may be performed as required.

When the (meth)acrylic acid recovered in the above step (C1) is reused as the (meth)acrylic acid used in the above step (A), new (meth)acrylic acid may be separately added and used. For the ratio of the recovered (meth)acrylic acid to the new (meth)acrylic acid when the new (meth)acrylic acid is separately added and used, preferably, 1 to 99% by mass of the new (meth)acrylic acid is mixed with respect to 100% by mass of the recovered (meth)acrylic acid.

The (meth)acrylic acid recovered in the above step (C1) may contain (meth)acrylic anhydride, but can be used as the (meth)acrylic acid used in the above step (A), as it is. The feed amount of the (meth)acrylic acid or the feed amount of the fatty acid anhydride represented by the above general formula (1) corresponding to the (meth)acrylic anhydride content may be adjusted as required.

In addition, a slight amount of the reaction product of the above alcohol and the fatty acid anhydride represented by the above general formula (1), produced as a by-product in the reaction in the above step (B), the (meth)acrylate, and the above alcohol, contained in the recovered (meth)acrylic acid, may be purified by a known method, such as distillation, adsorbent treatment, washing, or crystallization to further reduce their content.

The above steps (A) to (C), and the use of the recovered (meth)acrylic acid may be once, or may be repeated a plurality of times.

[Method for Storing (Meth)acrylic Anhydride]

A method for storing (meth)acrylic anhydride according to the present invention is characterized by allowing (meth)acrylic acid to coexist in an amount of 0.3 to 2 moles with respect to 1 mole of (meth)acrylic anhydride.

In the present invention, storage is defined as holding in a storage container or a reaction container in the form of a (meth)acrylic anhydride mixture for use in reactions with other raw materials. Examples thereof include a state in which an unpurified (meth)acrylic anhydride in the case of reacting unpurified (meth)acrylic anhydride with an alcohol to produce a (meth)acrylate is held in a storage container or a reaction container. Therefore, the storage does not include a state in which the composition changes largely, during the production of the (meth)acrylic anhydride, during the purification of the (meth)acrylic anhydride, during feeding, and the like. The storage container may be in any form, such as a storage tank, a drum, or a lorry used in factories or the like.

In the method for storing (meth)acrylic anhydride according to the present invention, the molar ratio of the (meth)acrylic acid to the (meth)acrylic anhydride in the reaction liquid is adjusted in the range of 0.3 to 2. By setting the above molar ratio to 0.3 or more, the stability of the (meth)acrylic anhydride is improved. In addition, as the above molar ratio increases, the stability of the (meth)acrylic anhydride is more improved. Therefore, the above molar ratio is preferably 0.5 or more. On the other hand, for the reason that as the amount of the (meth)acrylic acid increases, a container with a large volume becomes necessary during storage, the size of the reactor increases when the obtained reaction liquid as a (meth)acrylic anhydride raw material is reacted with an alcohol to produce a (meth)acrylate of the alcohol, the load for separating the obtained (meth)acrylate from the (meth)acrylic acid increases, and so on, the above molar ratio is 2 or less. The above molar ratio is preferably 1 or less, and more preferably 0.8 or less.

For the adjustment of the amount of the (meth)acrylic acid to satisfy the above molar ratio, (meth)acrylic acid in an amount corresponding to a shortage may be added, or the reaction conditions and the distillation conditions may be controlled so as to provide the desired composition when the (meth)acrylic anhydride is produced.

The storage temperature in the storage method in the present invention is preferably in the range of −30 to 120° C. in terms of the freezing point (melting point) of the (meth)acrylic anhydride or the (meth)acrylic acid, the storage temperature is more preferably 0° C. or more, and further preferably 10° C. or more. On the other hand, in terms of suppressing polymerization and side reactions, the storage temperature is more preferably 100° C. or less, and further preferably 90° C. or less.

The (meth)acrylic anhydride may be the reaction liquid at the completion of the reaction in which the catalyst is present, or one washed or purified by distillation, in the production method of the present invention. The one washed or purified by distillation contains little (meth)acrylic acid, and the stability decreases significantly. The storage method of the present invention is very effective for (meth)acrylic anhydride with such a composition.

In the storage method in the present invention, the type and amount of the metal compound contained in the (meth)acrylic anhydride are big factors of storage stability. The above metal compound is preferably a compound of a metal having a Pauling electronegativity of 1.0 or more, and more preferably a compound of a metal having a Pauling electronegativity of 1.5 or more, because of a small amount of undesirable side reaction products during the storage. The above metal compound is further preferably a compound of one or more metals selected from vanadium, manganese, iron, cobalt, nickel, copper, zinc, zirconium, and indium. Among them, compounds of cobalt, nickel, or indium are optimum. The metal compound may be present alone, or two or more of the metal compounds may be present. The metal compound is usually present in a form in which a salt of an inorganic acid, such as a sulfate, a chloride, a nitrate, a phosphate, or a borate; an organic acid salt, such as an acetate, a (meth)acrylate, or a sulfonate; or a complex salt, such as an acetylacetonate or a cyclopentadienyl complex, is dissolved.

The content of the metal compound is preferably 0.005 times moles or less, with respect to the (meth)acrylic anhydride, in terms of storage stability. For a similar reason, the content of the metal compound is more preferably 0.001 times moles or less, and further preferably 0.0005 times moles or less, with respect to the (meth)acrylic anhydride. The content of the metal compound is particularly preferably 0.0001 times moles or less because even unpurified (meth) acrylic anhydride can be sufficiently used as a reaction reagent. The content of the metal compound is preferably 0.000001 times moles or more, more preferably 0.000005 times moles or more, and further preferably 0.00001 times moles or more with respect to (meth)acrylic anhydride, in that side reactions can be decreased.

In the present invention, a polymerization inhibitor can also be used in the storage of the (meth)acrylic anhydride. The polymerization inhibitor may be one added at the stage of the reaction or the distillation during the production of the (meth) acrylic anhydride, or may be separately introduced into the storage container during the storage. For the polymerization inhibitor used, the above-described polymerization inhibitors inert to the acid anhydride and the (meth)acrylic acid are preferred.

Examples of the polymerization inhibitor that can be used include those similar to the polymerization inhibitors used in the step (A). One of these polymerization inhibitors may be used alone, or two or more of these polymerization inhibitors may be used in combination.

The amount of the polymerization inhibitor added is affected by its type and conditions, but is preferably in the range of 0.01 to 10000 ppm with respect to the weight of the storage liquid. In addition, the effect of preventing polymerization may be improved by bubbling a gas containing oxygen.

If a solvent is present, the purity decreases due to the impurities and the stabilizer contained in the solvent, the production of a reaction product of the (meth)acrylic anhydride and the solvent, and the like. Therefore, the storage is preferably performed without a solvent. A solvent and the like remaining when the apparatus is washed may be mixed, but they are not a problem if they are 10% or less by mass with respect to the reaction liquid.

EXAMPLES

The present invention will be described below in detail by Examples, but the present invention is not limited to these.

In the Examples, analysis and quantification were performed by gas chromatography (column: "DB-5" manufactured by J&B Scientific, with a length of 30 m, an inner diameter of 0.53 mm, and a film thickness of 3 μm, injection temperature: 200° C., detector temperature: 250° C., column temperature and time: the temperature was 60° C. for 1 minute, raised at 10° C./min, and held at 250° C.).

Example 1

918 g (9.0 mol) of acetic anhydride, 1705 g (19.8 mol) of methacrylic acid, 22.5 mg (0.00009 mol) of nickel acetate tetrahydrate as a catalyst, and 2.6 g of phenothiazine as a polymerization inhibitor were fed into a 3 L five-neck flask provided with a rectifying column (inner diameter: 35 mm, theoretical plate number: 10), a stirring blade, a thermometer, and an air-blowing tube. While the internal liquid in the flask was air-bubbled and stirred, the flask was heated in an oil bath. After the internal temperature reached 80° C., the internal temperature was held at 80° C. for 1 hour so that the composition of the reaction liquid reached equilibrium. After further 30 minutes, a vacuum pump was activated, with air bubbled, to start reducing the pressure. A total reflux state was created, with the temperature of the reaction liquid being 70° C., and the pressure in the flask being 6.4 kPa. Then, the distillate was extracted from the column top at a reflux ratio of 1.5, and this point was taken as the start of the reaction. After 8 hours, the reflux ratio was changed to 2.0, and the reaction was performed over 24 hours. During this time, 96 g of methacrylic acid in which 192 mg of phenothiazine was dissolved was supplied to the upper portion of the rectifying column for the prevention of polymerization in the column. This methacrylic acid descended in the rectifying column and was introduced into the flask. The temperature of the reaction liquid was gradually raised to 83° C., and the pressure in the flask was gradually lowered to 2.1 kPa. A distillate containing acetic acid as a main component was extracted from the column top of the rectifying column. The distillate was recovered by a cooling tube cooled to 15° C., and a trap immersed in liquid nitrogen. After the completion of the reaction, the reaction liquid was cooled.

During the reaction, the composition of the reaction liquid in the still and the distillate was analyzed by gas chromatography, and the quantification of methacrylic anhydride, a mixed anhydride, acetic anhydride, acetic acid, and methacrylic acid was performed.

The weight of the reaction liquid at the completion of the reaction was 1409 g, the composition was 80.6% by mass of methacrylic anhydride, 0% by mass of the mixed anhydride, 0% by mass of acetic anhydride, 0% by mass of acetic acid, and 13.8% by mass of methacrylic acid, and the yield of the methacrylic anhydride based on the acetic anhydride (calculated by dividing the number of moles of the methacrylic anhydride at the completion of the reaction by the number of moles of the acetic anhydride fed and multiplying the result by 100) was 81.9%. At this time, the molar ratio of the methacrylic acid to the methacrylic anhydride was 0.31.

The weight of the distillate was 1305 g, and the composition was 0.3% by mass of methacrylic anhydride, 2.6% by mass of the mixed anhydride, 8.6% by mass of acetic anhydride, 70.4% by mass of acetic acid, and 17.6% by mass of methacrylic acid.

From the result of the quantification, the total number of moles of the methacrylic anhydride, the mixed anhydride, and the acetic anhydride in the reaction liquid and the distillate was calculated. This value was divided by the total number of moles of the acetic anhydride fed to the flask, and the result was taken as anhydride balance. The anhydride balance at this time was 0.974. The anhydride balance was subtracted from 1, and the obtained value was multiplied by 100 and represented by percentage. The result was taken as a side reaction rate. The anhydride balance, the side reaction rate, and the gas chromatographic area ratio of compounds considered as Michael adducts of methacrylic anhydride are shown in Table 1.

Examples 2 to 8

A reaction was carried out as in Example 1, except that the type and amount of the catalyst were changed to those shown in Table 1. The molar ratio of the methacrylic acid to the methacrylic anhydride, the anhydride balance, the side reaction rate, and the gas chromatographic area ratio of compounds considered as Michael adducts of methacrylic anhydride are shown in Table 1.

Example 9

A reaction was carried out as in Example 1, except that the feed amount of the methacrylic acid was changed to 1858 g (21.6 mol). The molar ratio of the methacrylic acid to the methacrylic anhydride, the anhydride balance, the side reaction rate, and the gas chromatographic area ratio of compounds considered as Michael adducts of methacrylic anhydride are shown in Table 1.

Reference Example 1

A reaction was carried out under the same conditions as Example 1, except that a dropping funnel was attached to a 3 L five-neck flask, and 462 g (3.0 mol) of methacrylic anhydride purified by distillation was supplied after 12 hours from the start of the reaction. This methacrylic acid descended in the rectifying column and was introduced into the flask.

The weight of the reaction liquid at the completion of the reaction was 1867 g, and the composition was 82.8% by mass of methacrylic anhydride, 0.2% by mass of a mixed anhydride, 0% by mass of acetic anhydride, 0% by mass of acetic acid, and 10.8% by mass of methacrylic acid. At this time, the molar ratio of the methacrylic acid to the methacrylic anhydride was 0.23.

The weight of the distillate was 1308 g, and the composition was 0.7% by mass of methacrylic anhydride, 2.6% by mass of the mixed anhydride, 8.5% by mass of acetic anhydride, 70.4% by mass of acetic acid, and 17.3% by mass of methacrylic acid. The anhydride balance at this time was 0.956. The anhydride balance was subtracted from 1, and the obtained value was multiplied by 100 and represented by percentage. The result was taken as a side reaction rate. The molar ratio of the methacrylic acid to the methacrylic anhydride, the anhydride balance, the side reaction rate, and the gas chromatographic area ratio of compounds considered as Michael adducts of methacrylic anhydride are shown in Table 1.

Comparative Example 1

A reaction was carried out as in Reference Example 1, except that the catalyst and the amount of the catalyst were changed to those shown in Table 1. The molar ratio of the methacrylic acid to the methacrylic anhydride, the anhydride balance, the side reaction rate, and the gas chromatographic area ratio of compounds considered as Michael adducts of methacrylic anhydride are shown in Table 1.

Comparative Example 2

71.5 g (0.7 mol) of acetic anhydride, 172.2 g (2.0 mol) of methacrylic acid, 1.72 g (1% by mass with respect to the methacrylic acid) of sodium acetate as a catalyst, and 0.04 g of BHT as a polymerization inhibitor were fed into a 1 L five-neck flask provided with a rectifying column (inner diameter: 30 mm) packed with an amount of a column packing (Heli Pack No. 2) having the separation efficiency of 12 theoretical plates, a stirring blade, a thermometer, and an air-blowing tube. While the internal liquid in the flask was air-bubbled and stirred, the flask was heated in an oil bath. After the internal temperature reached 80° C., the internal temperature was held at 80° C. for 1 hour so that the composition of the reaction liquid reached equilibrium. Then, a vacuum pump was activated, with air bubbled, to start reducing the pressure. The pressure was further reduced, and a total reflux state was created, with the temperature of the reaction liquid being 80° C. Then, the distillate was extracted from the column top at a reflux ratio of 4, and this point was taken as the start of the reaction. The pressure was reduced to 4.0 kPa so that the amount of vapor was constant. After 7 hours, the reaction was completed. During this time, 14 ml of acetic acid in which 5% Topanol A and 5% HQ were dissolved was supplied to the upper portion of the rectifying column for the prevention of polymerization in the column. A distillate containing acetic acid as a main component was extracted from the column top of the rectifying column, and recovered by a cooling tube cooled to 15° C., and a trap immersed in liquid nitrogen. After the completion of the reaction, the reaction liquid was cooled.

During the reaction, the composition of the reaction liquid in the still and the distillate was analyzed by gas chromatography, and the quantification of methacrylic anhydride, a mixed anhydride, acetic anhydride, acetic acid, and methacrylic acid was performed.

The weight of the reaction liquid at the completion of the reaction was 121.4 g, and the composition was 80.1% by mass of methacrylic anhydride, 1.7% by mass of the mixed anhydride, 0.1% by mass of acetic anhydride, 0.6% by mass of acetic acid, and 9.8% by mass of methacrylic acid. In the analysis by gas chromatography, a large number of peaks considered as those of compounds in which one or two acetic acids or methacrylic acids were added to methacrylic anhydride by Michael addition were detected.

The yield of the methacrylic anhydride based on the acetic anhydride (calculated by dividing the number of moles of the methacrylic anhydride at the completion of the reaction by the number of moles of the acetic anhydride fed and multiplying the result by 100) was 90.1%. At this time, the molar ratio of the methacrylic acid to the methacrylic anhydride was 0.22.

The weight of the distillate was 128.5 g, and the composition was 0.1% by mass of methacrylic anhydride, 0.2% by mass of the mixed anhydride, 0.9% by mass of acetic anhydride, 70.0% by mass of acetic acid, and 28.5% by mass of methacrylic acid.

From the result of the quantification, the total number of moles of the methacrylic anhydride, the mixed anhydride, and the acetic anhydride in the reaction liquid and the distillate was calculated. This value was divided by the total number of moles of the acetic anhydride fed to the flask, and the result was taken as anhydride balance. The anhydride balance at this time was 0.946. The anhydride balance was subtracted from 1, and the obtained value was multiplied by 100 and represented by percentage. The result was taken as a side reaction rate. The molar ratio of the methacrylic acid to the methacrylic anhydride, the anhydride balance, the side reaction rate, and the gas chromatographic area ratio of compounds considered as Michael adducts of methacrylic anhydride are shown in Table 1.

TABLE 1

|  | Catalyst | Amount of catalyst with respect to acetic anhydride (mol/mol) | Molar ratio of methacrylic acid to methacrylic anhydride | Anhydride balance | Side reaction rate (%) | Gas chromatographic area ratio of compounds considered as Michael adducts of methacrylic anhydride |
|---|---|---|---|---|---|---|
| Ex. 1 | Nickel acetate tetrahydrate | 0.00001 | 0.31 | 0.974 | 2.6 | 0.018 |
| Ex. 2 | Cobalt acetate tetrahydrate | 0.00001 | 0.31 | 0.978 | 2.2 | 0.016 |

TABLE 1-continued

| | Catalyst | Amount of catalyst with respect to acetic anhydride (mol/mol) | Molar ratio of methacrylic acid to methacrylic anhydride | Anhydride balance | Side reaction rate (%) | Gas chromatographic area ratio of compounds considered as Michael adducts of methacrylic anhydride |
|---|---|---|---|---|---|---|
| Ex. 3 | Nickel acetate tetrahydrate | 0.0001 | 0.32 | 0.975 | 2.5 | 0.019 |
| Ex. 4 | Indium acetate | 0.0001 | 0.31 | 0.973 | 2.7 | 0.019 |
| Ex. 5 | Manganese acetate | 0.0001 | 0.32 | 0.969 | 3.1 | 0.025 |
| Ex. 6 | Magnesium acetate | 0.0001 | 0.32 | 0.962 | 3.8 | 0.026 |
| Ex. 7 | Lithium acetate | 0.0001 | 0.33 | 0.960 | 4.0 | 0.029 |
| Ex. 8 | Nickel acetate tetrahydrate | 0.001 | 0.32 | 0.971 | 2.9 | 0.020 |
| Ex. 9 | Nickel acetate tetrahydrate | 0.00001 | 0.54 | 0.978 | 2.2 | 0.018 |
| Ref. Ex. 1 | Nickel acetate tetrahydrate | 0.00001 | 0.23 | 0.956 | 4.4 | 0.021 |
| Com. Ex. 1 | Sodium acetate | 0.0001 | 0.26 | 0.941 | 5.9 | 0.049 |
| Com. Ex. 2 | Sodium acetate | 0.02 | 0.22 | 0.946 | 5.4 | 0.071 |

Example 10

Figure 1:
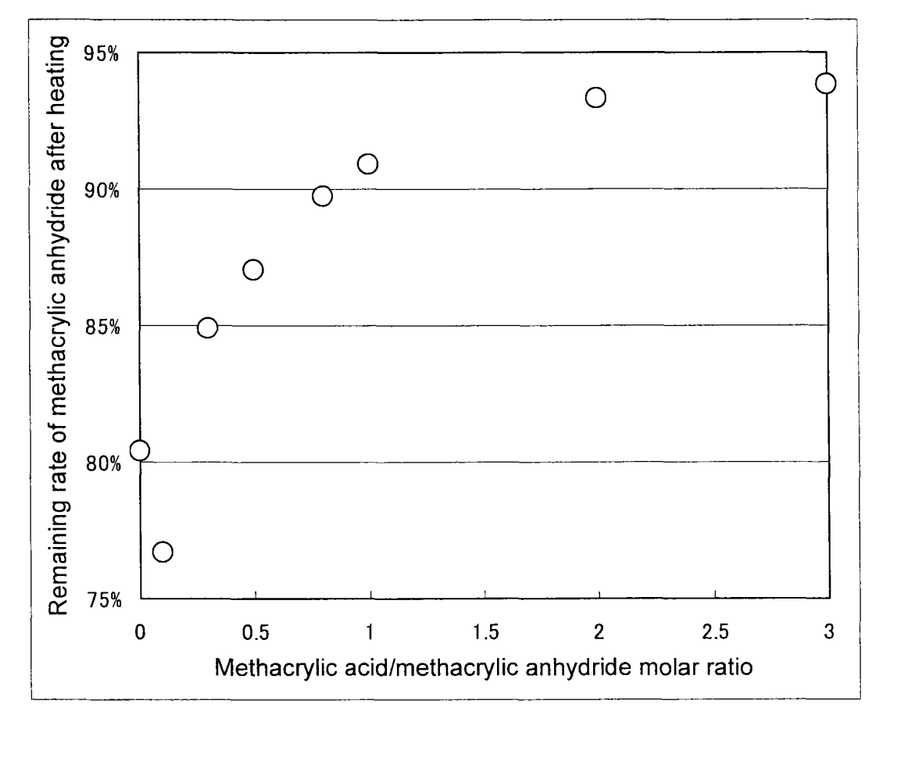
FIG. 1 is a diagram showing the remaining rate of methacrylic anhydride after heating with respect to the molar ratio of methacrylic acid to methacrylic anhydride.

30.8 g (0.2 mol) of methacrylic anhydride purified by distillation was placed in a pressure-resistant sealed container, and further, 5.2 g (0.06 mol) of methacrylic acid and 30 mg of phenothiazine were placed. The container was sealed, and the mixture was heated and stirred at 80° C. for 24 hours, while being shielded from light. After cooling, the reaction liquid was quantitatively analyzed by gas chromatography. As a result, the methacrylic anhydride remaining in the reaction liquid was 84.9% of the methacrylic anhydride before the heating (taken as a remaining rate). The value obtained by subtracting the remaining rate from 100% was taken as a by-product production rate. The remaining rate is shown in FIG. 1, and the molar ratio of the methacrylic acid to the methacrylic anhydride before the heat treatment, the remaining rate, the by-product production rate, and the gas chromatographic area ratio of compounds considered as Michael adducts of methacrylic anhydride are shown in Table 2.

Comparative Example 3

30.8 g (0.2 mol) of methacrylic anhydride purified by distillation and 30 mg of phenothiazine were placed in a pressure-resistant sealed container. The container was sealed, and the mixture was heated and stirred at 80° C. for 24 hours, while being shielded from light. After cooling, the reaction liquid was quantitatively analyzed by gas chromatography. As a result, the content of the methacrylic anhydride remaining in the reaction liquid was 80.4% of the methacrylic anhydride before the heating (taken as a remaining rate). The value obtained by subtracting the remaining rate from 100% was taken as a by-product production rate. The remaining rate is shown in FIG. 1, and the molar ratio of the methacrylic acid to the methacrylic anhydride before the heat treatment, the remaining rate, the by-product production rate, and the gas chromatographic area ratio of compounds considered as Michael adducts of methacrylic anhydride are shown in Table 2. In addition, the area percentage of each compound as a result of analysis by gas chromatography (represented by retention time except for the methacrylic acid and the methacrylic anhydride) is shown in Table 3.

Comparative Example 4

Operations were performed as in Example 10, except that the amount of the methacrylic acid was changed to an amount providing a ratio of 0.1 moles of the methacrylic acid to 1 mole of the methacrylic anhydride. The results are shown in FIG. 1 and Table 2.

Examples 11 to 14

Operations were performed as in Example 10, except that the amount of the methacrylic acid was changed to an amount providing a ratio of 0.5 moles (Example 11), 0.8 moles (Example 12), 1.0 mole (Example 13), or 2.0 moles (Example 14) of the methacrylic acid to 1 mole of the methacrylic anhydride. The results are shown in FIG. 1 and Table 2. In addition, for Example 13, the area percentage of each compound as a result of analysis by gas chromatography (represented by retention time except for the methacrylic acid and the methacrylic anhydride) is shown in Table 3. From Table 3, it is seen that the produced impurities are totally different.

Reference Example 2

Operations were performed as in Example 10, except that the amount of the methacrylic acid was changed to an amount providing a ratio of 3.0 moles of the methacrylic acid to 1 mole of the methacrylic anhydride. The results are shown in FIG. 1 and Table 2.

From FIG. 1, it is seen that by adding methacrylic acid with respect to methacrylic anhydride at a molar ratio of 0.3 or more, the remaining rate of the methacrylic anhydride after heating is improved. In addition, as the molar ratio of the methacrylic acid to the methacrylic anhydride is increased, the remaining rate of the methacrylic anhydride is further improved, and therefore, it is seen that by adding methacrylic acid with respect to methacrylic anhydride at a molar ratio of 0.3 or more, an effective effect is obtained in the storage of the methacrylic anhydride. When the molar ratio is more than 2, the improvement in remaining rate is small, and it is seen that a molar ratio of up to 2 is sufficient.

TABLE 2

| | Molar ratio of methacrylic acid to methacrylic anhydride before heat treatment | Remaining rate of methacrylic anhydride (%) | By-product production rate (%) | Gas chromatographic area ratio of compounds considered as Michael adducts of methacrylic anhydride |
|---|---|---|---|---|
| Com. Ex. 3 | 0 | 80.4 | 19.6 | 0.018 |
| Com. Ex. 4 | 0.1 | 76.7 | 23.3 | 0.060 |
| Ex. 10 | 0.3 | 84.9 | 15.1 | 0.055 |
| Ex. 11 | 0.5 | 87.0 | 13.0 | 0.055 |
| Ex. 12 | 0.8 | 89.7 | 10.3 | 0.058 |
| Ex. 13 | 1.0 | 90.9 | 9.1 | 0.063 |
| Ex. 14 | 2.0 | 93.3 | 6.7 | 0.062 |
| Ref. Ex. 2 | 3.0 | 93.6 | 6.4 | 0.051 |

TABLE 3

| Compound name (number represents retention time (minutes)) | Com. Ex. 3 | Ex. 13 |
|---|---|---|
| Methacrylic acid | 0.8% | 32.2% |
| Methacrylic anhydride | 92.5% | 63.2% |
| 11.3 | 0.6% | 0.3% |
| Compound considered as Michael adduct | 0.3% | 0.2% |
| Compound considered as Michael adduct | 0.4% | 0.1% |
| 14.7 | 0.2% | 0% |
| 15.1 | 0.5% | 0% |
| 15.4 | 0.5% | 0% |
| 15.7 | 0.4% | 0% |
| 15.9 | 0.5% | 0% |
| 16.2 | 0.4% | 0% |
| 16.4 | 0.5% | 0% |
| 16.6 | 0.3% | 0% |
| 16.7 | 0.3% | 0% |
| 17.1 | 0.3% | 0% |
| 17.4 | 0.2% | 0% |
| Compound considered as Michael adduct | 0.5% | 1.7% |
| Compound considered as Michael adduct | 0.5% | 1.9% |
| 21.6 | 0% | 0.2% |
| 21.8 | 0% | 0.1% |

Example 15

Operations were performed as in Example 13, except that 0.002 mmol of nickel acetate tetrahydrate was added. The molar ratio of the methacrylic acid to the methacrylic anhydride before the heat treatment, the remaining rate, the by-product production rate, and the gas chromatographic area ratio of compounds considered as Michael adducts of methacrylic anhydride are shown in Table 4.

Example 16

Operations were performed as in Example 15, except that the amount of the nickel acetate tetrahydrate was changed to 0.02 mmol. The molar ratio of the methacrylic acid to the methacrylic anhydride before the heat treatment, the remaining rate, the by-product production rate, and the gas chromatographic area ratio of compounds considered as Michael adducts of methacrylic anhydride are shown in Table 4.

Example 17

Operations were performed as in Example 15, except that the nickel acetate tetrahydrate was changed to 0.002 mmol of cobalt acetate tetrahydrate. The molar ratio of the methacrylic acid to the methacrylic anhydride before the heat treatment, the remaining rate, the by-product production rate, and the gas chromatographic area ratio of compounds considered as Michael adducts of methacrylic anhydride are shown in Table 4.

Example 18

Operations were performed as in Example 15, except that the nickel acetate tetrahydrate was changed to 0.002 mmol of indium acetate. The molar ratio of the methacrylic acid to the methacrylic anhydride before the heat treatment, the remaining rate, the by-product production rate, and the gas chromatographic area ratio of compounds considered as Michael adducts of methacrylic anhydride are shown in Table 4.

Reference Example 3

Operations were performed as in Example 15, except that the nickel acetate tetrahydrate was changed to 0.002 mmol of sodium carbonate. The molar ratio of the methacrylic acid to the methacrylic anhydride before the heat treatment, the remaining rate, the by-product production rate, and the gas chromatographic area ratio of compounds considered as Michael adducts of methacrylic anhydride are shown in Table 4.

Reference Example 4

Operations were performed as in Example 15, except that the nickel acetate tetrahydrate was changed to 0.02 mmol of sodium carbonate. The molar ratio of the methacrylic acid to the methacrylic anhydride before the heat treatment, the remaining rate, the by-product production rate, and the gas chromatographic area ratio of compounds considered as Michael adducts of methacrylic anhydride are shown in Table 4.

TABLE 4

| | Molar ratio of methacrylic acid to methacrylic anhydride before heat treatment | Metal compound | Amount of metal compound with respect to methacrylic anhydride (mol/mol) | Remaining rate of methacrylic anhydride (%) | By-product production rate (%) | Gas chromatographic area ratio of compounds considered as Michael adducts of methacrylic anhydride |
|---|---|---|---|---|---|---|
| Ex. 15 | 1.0 | Nickel acetate tetrahydrate | 0.00001 | 91.9 | 8.1 | 0.051 |
| Ex. 16 | 1.0 | Nickel acetate tetrahydrate | 0.0001 | 91.4 | 8.6 | 0.052 |
| Ex. 17 | 1.0 | Cobalt acetate tetrahydrate | 0.00001 | 92.1 | 7.8 | 0.048 |
| Ex. 18 | 1.0 | Indium acetate | 0.00001 | 91.5 | 8.5 | 0.052 |

TABLE 4-continued

| | Molar ratio of methacrylic acid to methacrylic anhydride before heat treatment | Metal compound | Amount of metal compound with respect to methacrylic anhydride (mol/mol) | Remaining rate of methacrylic anhydride (%) | By-product production rate (%) | Gas chromatographic area ratio of compounds considered as Michael adducts of methacrylic anhydride |
|---|---|---|---|---|---|---|
| Ref. Ex. 3 | 1.0 | Sodium carbonate | 0.00001 | 87.9 | 12.1 | 0.083 |
| Ref. Ex. 4 | 1.0 | Sodium carbonate | 0.0001 | 84.2 | 15.8 | 0.121 |

Example 19

Step (A)

918 g (9.0 mol) of acetic anhydride, 1705 g (19.8 mol) of methacrylic acid, 22.5 mg (0.00009 mol) of nickel acetate tetrahydrate as a catalyst, and 2.6 g of phenothiazine as a polymerization inhibitor were fed into a 3 L five-neck flask provided with a rectifying column (inner diameter: 35 mm, theoretical plate number: 10), a stirring blade, a thermometer, and an air-blowing tube. While the internal liquid in the flask was air-bubbled and stirred, the flask was heated in an oil bath. After the internal temperature reached 80° C., the internal temperature was held at 80° C. for 1 hour so that the composition of the reaction liquid reached equilibrium. After further 30 minutes, a vacuum pump was activated, with air bubbled, to start reducing the pressure. A total reflux state was created, with the temperature of the reaction liquid being 70° C., and the pressure in the flask being 6.4 kPa. Then, the distillate was extracted from the column top at a reflux ratio of 1.5, and this point was taken as the start of the reaction. After 8 hours, the reflux ratio was changed to 2.0, and the reaction was performed over 24 hours. During this time, 96 g of methacrylic acid in which 192 mg of phenothiazine was dissolved was supplied to the upper portion of the rectifying column for the prevention of polymerization in the rectifying column. The temperature of the reaction liquid was gradually raised to 83° C., and the pressure in the flask was gradually lowered to 2.1 kPa. A distillate containing acetic acid as a main component was extracted from the column top of the rectifying column. The distillate was recovered by a cooling tube cooled to 15° C., and a trap immersed in liquid nitrogen. After the completion of the reaction, the reaction liquid was cooled.

The weight of the reaction liquid at the completion of the reaction was 1409 g, the composition was 80.6% by mass of methacrylic anhydride, 0.1% by mass of a mixed anhydride, 0% by mass of acetic anhydride, 0% by mass of acetic acid, and 13.8% by mass of methacrylic acid, and the yield of the methacrylic anhydride based on the acetic anhydride (calculated by dividing the number of moles of the methacrylic anhydride at the completion of the reaction by the number of moles of the acetic anhydride fed and multiplying the result by 100) was 81.9%.

Step (B)

696 g (7.4 mol) of phenol and 35 g (0.35 mol) of 98 mass % sulfuric acid were added to the 3 L flask containing the above reaction liquid, and the mixture was heated to 80° C., with air bubbled, and then reacted for 8 hours. The methacrylic anhydride disappeared completely. The yield of phenyl methacrylate based on the methacrylic anhydride (calculated by dividing the number of moles of the phenyl methacrylate at the completion of the reaction by the number of moles of the methacrylic anhydride and multiplying the result by 100) at this time was 99.1%, and the contained methacrylic acid was 823 g.

(Step (C1))

A vacuum pump was activated, with air bubbled, to start reducing the pressure. A total reflux state was created, with the temperature of the reaction liquid being 80° C., and the pressure in the flask being 2.1 kPa. Then, the distillate was extracted from the column top at a reflux ratio of 1.5. The distillate was recovered by a cooling tube cooled to 15° C., and a trap immersed in liquid nitrogen. With the pressure remaining the same, the temperature was raised to 115° C. When 777 g of the distillate was extracted, the recovery was completed. During this time, 32 g of methacrylic acid in which 64 mg of phenothiazine was dissolved was supplied to the upper portion of the rectifying column for the prevention of polymerization in the rectifying column. The composition of the distillate at this time was 99.2% by mass of methacrylic acid, 0.1% by mass of phenyl methacrylate, and 0.6% by mass of phenol, and the recovery rate of the methacrylic acid (calculated by dividing the number of moles of the methacrylic acid in the distillate by the number of moles of the methacrylic acid in the reaction liquid and multiplying the result by 100) was 90.1%.

(Step (C2))

The reaction liquid was removed from the flask and dissolved in 2 L of hexane, and the hexane solution was washed twice with 2 L of pure water. The hexane solution was washed twice with 2 L of a 7 mass % aqueous sodium carbonate solution, then washed once with 2 L of a 1 mass % aqueous sodium hydroxide solution, and washed twice with 2 L of pure water. The hexane solution was concentrated by an evaporator, and subjected to simple distillation at a temperature of 70 to 120° C. and a pressure of 300 to 400 Pa. As a result of recovering all fractions, 1010 g (6.2 mol) of phenyl methacrylate having a purity of 99.7% by mass was obtained. The phenyl acetate content at this time was 0.01% or less by mass (the detection limit or less).

Use of Recovered Methacrylic Acid

Using 770 g of the distillate containing the recovered methacrylic acid, to which 942 g of methacrylic acid was newly added, for a methacrylic acid raw material, the steps (A) to (C2) for producing new phenyl methacrylate were repeated again.

In the step (C1) for producing new phenyl methacrylate, the recovery rate of the methacrylic acid was 90.5%, and the composition was 99.2% by mass of methacrylic acid, 0.1% by mass of phenyl methacrylate, and 0.6% by mass of phenol. The phenyl methacrylate obtained in the step (c2) for producing new phenyl methacrylate was 1008 g (6.2 mol), the purity was 99.9% by mass, and the phenyl acetate content was 0.01% or less by mass (the detection limit or less).

Example 20

Reactions were carried out as in Example 19, except that in the operation of the step (B), the catalyst was changed to sodium carbonate, and the amount of the phenol was 668 g (7.1 mol). As a result, the yield of the phenyl methacrylate in the step (B) was 94.7%.

In the step (C1), the viscosity of the reaction liquid increased in midstream, and therefore, the recovery rate of the methacrylic acid was 86.9%, and the composition was 99.1% by mass of methacrylic acid, 0.1% by mass of phenyl methacrylate, and 0.7% by mass of phenol.

In the step (C2), 970 g (6.0 mol) of phenyl methacrylate having a purity of 99.7% by mass was obtained. The phenyl acetate content at this time was 0.01% or less by mass (the detection limit or less).

In the step (C1) for producing new phenyl methacrylate, the recovery rate of the methacrylic acid was 47.5%, and the composition was 99.0% by mass of methacrylic acid, 0.1% by mass of phenyl methacrylate, and 0.7% by mass of phenol.

The phenyl methacrylate obtained in the step (C2) for producing new phenyl methacrylate was 961 (5.9 mol), the purity was 99.8% by mass, and the phenyl acetate content was 0.01% or less by mass.

Example 21

Operations and reactions were performed as in Example 19, except that in the step (B), the amount of the phenol was 706 g (7.5 mol) so that the content of the phenyl methacrylate in the distilled methacrylic acid was 0.1% by mass, and the content of the phenol was 2.5% by mass.

The phenyl methacrylate obtained in the step (C2) for producing new phenyl methacrylate was 1003 g (6.2 mol), the purity was 99.6% by mass, and the phenyl acetate content was 0.2% by mass.

Comparative Example 5

Operations and reactions were performed as in Example 19, except that in the step (B), the amount of the phenol was 715 g (7.6 mol) so that the content of the phenyl methacrylate in the distilled methacrylic acid was 0.1% by mass, and the content of the phenol was 3.8% by mass.

The phenyl methacrylate obtained in the step (C2) for producing new phenyl methacrylate was 1001 g (6.2 mol), the purity was 99.0% by mass, and the phenyl acetate content was 0.8% by mass.

INDUSTRIAL APPLICABILITY

According to the production method of the present invention, (meth)acrylic anhydride can be produced with high yield. In addition, by reacting (meth)acrylic anhydride with alcohols by the method of the present invention, (meth)acrylates with high yield and high purity can be produced. Further, according to the storage method of the present invention, the degradation of (meth)acrylic anhydride during storage can be suppressed.

The invention claimed is:

1. A method for storing (meth)acrylic anhydride, the method comprising:
   adjusting a molar amount of (meth)acrylic acid in a mixture with the (meth)acrylic anhydride to be in a range of from 0.3 to 2 with respect to 1 mole of the (meth)acrylic anhydride.

2. The method according to claim 1, wherein the (meth)acrylic anhydride is stored in the presence of a metal having a Pauling electronegativity of 1.0 or more.

3. The method according to claim 2, wherein the metal is at least one selected from the group consisting of nickel, cobalt, and indium.

4. The method according to claim 1, wherein the (meth)acrylic anhydride is stored in the absence of a solvent.

* * * * *